(12) United States Patent
Shang et al.

(10) Patent No.: US 7,889,345 B2
(45) Date of Patent: Feb. 15, 2011

(54) METHOD AND SYSTEM FOR DETECTING THE LEVEL OF ANESTHESIA AGENT IN AN ANESTHESIA VAPORIZER

(76) Inventors: Allan Bruce Shang, 5625 Chimney Swift Dr., Wake Forrest, NC (US) 27587; Eugene William Moretti, 9 Copper Hill Ct., Durham, NC (US) 27713; Lewis Roger Hodgins, 201 Turquoise Cr. Dr., Cary, NC (US) 27513

( * ) Notice: Subject to any disclaimer, the term of this patent is extended or adjusted under 35 U.S.C. 154(b) by 479 days.

(21) Appl. No.: 11/809,453

(22) Filed: Jun. 2, 2007

(65) Prior Publication Data
US 2008/0236580 A1    Oct. 2, 2008

Related U.S. Application Data

(60) Provisional application No. 60/920,513, filed on Mar. 28, 2007.

(51) Int. Cl.
*G01N 21/00* (2006.01)
*A61M 16/00* (2006.01)

(52) U.S. Cl. .............. 356/440; 128/203.12; 128/203.14

(58) Field of Classification Search ....................... None
See application file for complete search history.

(56) References Cited

U.S. PATENT DOCUMENTS

| | | | | |
|---|---|---|---|---|
| 3,452,208 | A | * | 6/1969 | Giltinan ...................... 250/577 |
| 3,908,441 | A | * | 9/1975 | Virloget ...................... 250/577 |
| 2005/0105095 | A1 | * | 5/2005 | Pesach et al. ............... 356/432 |
| 2006/0110292 | A1 | * | 5/2006 | Deverse et al. ............. 422/68.1 |

FOREIGN PATENT DOCUMENTS

EP    1715304 A1 * 10/2006
SU    1668871 A1 * 8/1991

* cited by examiner

*Primary Examiner*—Gregory J Toatley
*Assistant Examiner*—Juan D Valentin
(74) *Attorney, Agent, or Firm*—Bryan A. Shang

(57) ABSTRACT

A method of detecting a level of anesthetic agent in an anesthesia vaporizer is disclosed. The anesthetic agent forms a column of liquid within an external indicator; the method projects a beam of light into the external indicator. The method further receives the beam of light after the beam of light has traveled through the column of liquid, and detects when the level of anesthetic agent drops below a predetermined level.

21 Claims, 7 Drawing Sheets

REFLECTANCE METHOD

METHOD AND SYSTEM FOR DETECTING THE LEVEL OF ANESTHESIA AGENT IN AN ANESTHESIA VAPORIZER

CROSS REFERENCE TO RELATED APPLICATION

This application claims the priority of U.S. provisional patent application Ser. No. 60/920,513 filed on Mar. 28, 2007, entitled "A Method and System for Detecting Levels Of Anesthesia Agents," the contents of which are relied upon and incorporated herein by reference in their entirety, and the benefit of priority under 35 U.S.C. 119(e) is hereby claimed.

FIELD OF INVENTION

The present invention relates to the measuring of inhaled anesthetic agents, and more particularly to techniques for measuring the level of an anesthetic agent in an anesthesia vaporizer.

BACKGROUND

Anesthesia in various forms has been used in medicine for centuries. The Incas used anesthesia to allow Shamans to drill into the heads of patients to let the bad spirits escape. There have also been reported uses of anesthesia in the Far East during the $10^{th}$ century to provide pain relief for birthing. Anesthesia has evolved from herbal concoctions to gas and vapor mixtures. During the $19^{th}$ century, various gaseous mixtures were being used for tooth extraction by dentists. Nitrous oxide had been discovered in the late 1700's but was not used for medical purposes until the mid 1800's. Dentists also started using diethyl ether to numb their patients before performing procedures. As dentistry evolved, other types of anesthetic agents such as chloroform were discovered. The use of anesthetic agents soon spread to other practices of medicine and was being widely used in surgical procedures towards the end of the $19^{th}$ century.

Inhaled anesthetic agents are unique among anesthetic drugs because they are introduced into and removed out of the body through the patient's lungs. One advantage of using inhaled anesthetics is the favorable pharmacokinetic properties (rapid onset and rapid recovery), which allow the anesthesia practitioner to quickly and effectively adjust the anesthetic depth of the patient.

In order to effectively use an inhaled anesthetic, special machines were developed to regulate the introduction of the inhaled anesthetic into the patient. One such machine is the anesthesia agent vaporizer, which is commonly referred to in the art as a "vaporizer". Typically the vaporizer is calibrated to introduce a percentage of inhaled anesthetic agents per percentage of volume. Different types of inhaled anesthetic agents have been developed, with each of the various anesthetic agents having unique properties. In order to effectively deliver the proper amount of inhaled anesthetic agent, vaporizers are typically calibrated for a specific anesthetic agent.

Associated with the delivery of inhaled anesthetics to the patient are various alarm systems which were developed in response to specific preventable patient complications. Disconnect alarms were developed after it was realized that deaths and serious complications arose because anesthesia practitioners sometimes failed to recognize that their patients were not being ventilated. As a result oxygen sensors were introduced to prevent death and serious injuries to patients from the unrecognized administration of hypoxic or anoxic gas mixtures. Oxygen pressure alarms were also introduced after it was realized that death and other serious patient complications have arisen when there was an unrecognized loss of oxygen delivery to the anesthesia machine and thus to the patient. In each of these cases, the alarm systems are designed to bring to the attention of the practitioner a potentially harmful situation before actual injury can occur.

Recall of painful events during anesthesia and surgery is another such preventable complication. Recall of intraoperative events occurs in approximately 0.1% of all general anesthetics. Many of these patients experience devastating psychological consequences such as PTSD (post traumatic stress disorder), and painful recall is one of the leading causes for malpractice claims against anesthesiologists. Greater than 40% of all recall events are related to equipment malfunctions. These malfunctions may result from a failure to deliver anesthetic gases (agent) to the patient. One such malfunction is an empty anesthetic agent vaporizer. A majority of all such recall events are related to an undetected empty vaporizer.

On the anesthesia vaporizer, there typically exists a clear tube which reflects the amount of anesthesia agent remaining in the vaporizer. The clear tube may be difficult to see especially in low light conditions. Additionally, the anesthesia practitioner may be distracted and not paying attention to the amount of anesthetic agent reflected in the clear tube. Thus there exists a need in the industry to have an alarm system that notifies the anesthesia practitioner when the level of anesthesia agent reaches a predetermined level, allowing the anesthesia practitioner to refill or replace the vaporizer.

SUMMARY

The present invention recognizes this need and discloses a way of determining the level of anesthetic agent present in an anesthesia vaporizer.

A method of detecting a level of anesthetic agent in an anesthesia vaporizer is disclosed. The anesthetic agent forms a column of liquid within an external indicator, the method projects a beam of light into the external indicator. The method further receives the beam of light after the beam of light has traveled through the column of liquid, and detects when the level of anesthetic agent drops below a predetermined level.

An apparatus for detecting a level of an anesthetic agent in an anesthesia vaporizer when the apparatus is coupled to an external indicator of the anesthesia vaporizer is disclosed. The apparatus has a light source for emitting a beam of light into the external indicator and a light receptor for receiving the beam of light after the beam of light has traveled through the external indicator. The apparatus also has a detection logic circuit for detecting when the beam of light is altered when the level of the anesthesia agent reaches a predetermined level.

An anesthesia vaporizer is disclosed. The anesthesia vaporizer has an external indicator, the external indicator having a column of liquid anesthetic agent, the column of liquid anesthetic agent is indicative of the level of anesthetic agent contained within the anesthesia vaporizer. The anesthesia vaporizer also has a light source which emits a beam of light, the light source being coupled to the external indicator and a light receptor, the light receptor configured to receive the beam of light after the beam of light travels through the external indicator. The anesthesia vaporizer has a detection logic circuit, the detection logic circuit detecting when the column of liquid anesthetic agent reaches a predetermined level.

DETAILED DESCRIPTION

Figure 1:
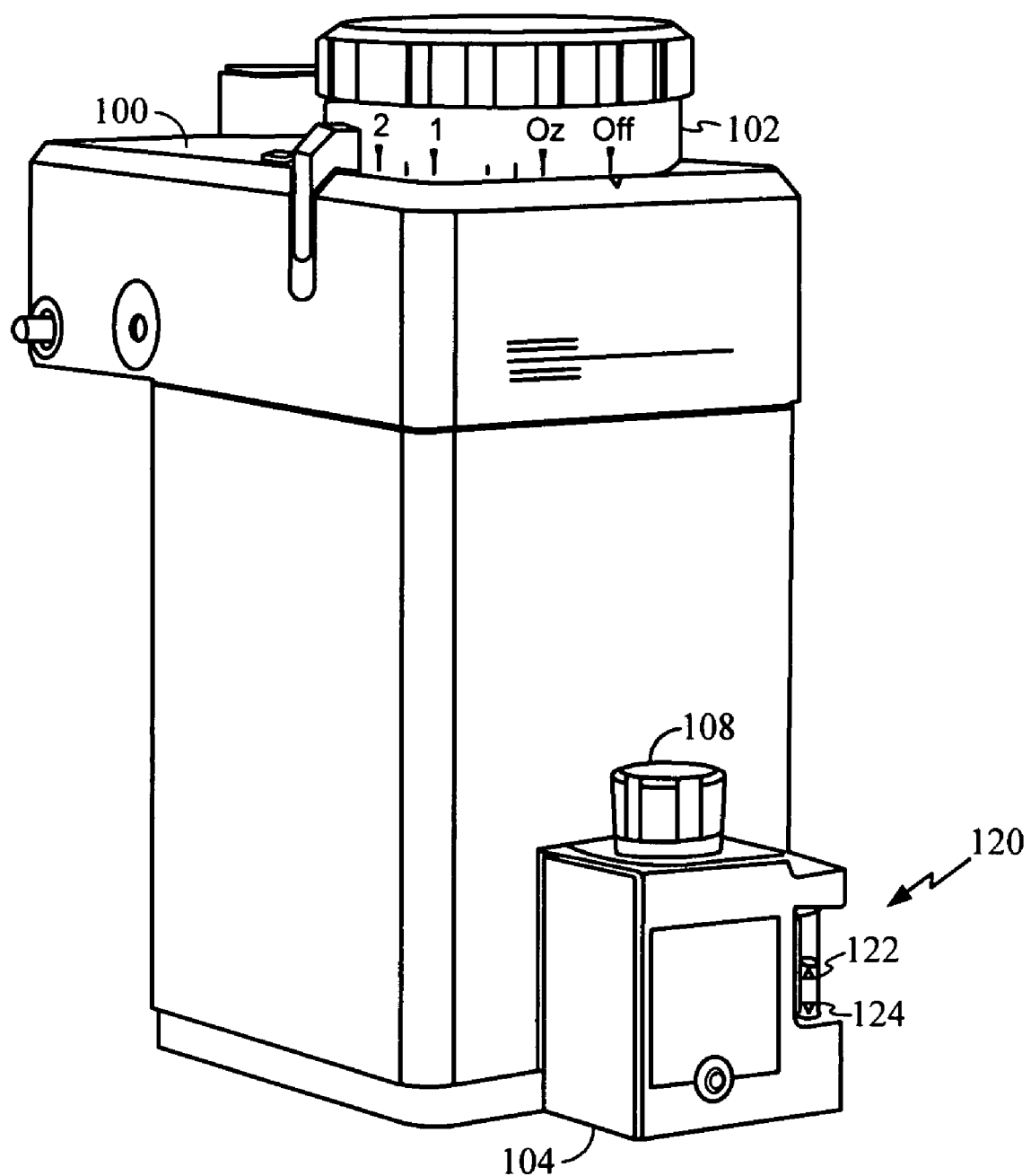
FIG. 1 displays a Tec-4 anesthesia vaporizer.

The following detailed description of preferred embodiments refers to the accompanying drawings, which illustrate specific embodiments of the invention. In the discussion that follows, specific systems and techniques for monitoring the level of anesthetic agents are used as examples. Other embodiments having different structures and operations for monitoring and alarming of anesthesia vaporizers do not depart from the scope of the present invention.

Inhaled anesthetics, also known in the art as volatile anesthetics, are a class of liquid halogenated ethers that are vaporized in order to be administered to patients. The inhaled anesthetics are typically given to patients requiring surgery which produce a lowering of consciousness, commonly known as general anesthesia. General anesthesia can be defined as a reversible depression of the central nervous system sufficient to permit surgery to be performed without movement, obvious distress, or recall. Prior to the mid-nineteenth century, surgical procedures were performed on a limited basis because there were no safe and effective anesthetic agents. Between 1842 and 1847 Crawford Long and W. T. G. Morton demonstrated that inhalation of diethyl ether could produce general anesthesia. During this same time period, Horace Wells demonstrated that nitrous oxide, and J. Y. Simpson demonstrated that chloroform could also produce general anesthesia. The incorporation of these inhaled anesthetics into clinical medical practice helped spawn the development of surgery.

Chloroform and diethyl ether had major limitations including flammability, unfavorable pharmacokinetics (slow onset and slow recovery), and other adverse side effects. A vigorous search for a better inhaled anesthetic produced Halothane, a halogenated alkane introduced in the 1950's. This was the first nonflammable and potent inhaled anesthetic agent. Following this, a series of halogenated short-chain ethers have been introduced with improved pharmacokinetic and side effect profiles; isoflurane, sevoflurane, and desflurane are anesthetic agents currently in clinical use. The inhalational agents remain the mainstay of the pharmacologic armamentarium used by anesthesia providers to deliver general anesthesia.

The volatile anesthetics are provided in liquid form in amber-colored bottles to minimize reaction with light. Halothane contains 0.01% thymol as a stabilizer; isoflurane, sevoflurane, and desflurane do not contain such additives. Modern anesthesia practice requires an anesthesia machine for safe and accurate delivery of inhaled anesthetics. Attached monitors and alarms allow quantification of anesthetic, oxygen and carbon dioxide concentrations and detection of physiologic side effects produced by inhaled agents. Anesthesia machines regulate oxygen and nitrous oxide cylinder pressures with specific flow meters controlling the flow of each gas (flow depends on the viscosity and density of the gas.) Oxygen and nitrous oxide combine and flow through a common manifold. The oxygen and nitrous oxide gas mixture may be directed to a vaporizer to pick up a precise amount of volatile agent before exiting the machine at a common gas outlet. The inhaled gases are delivered to a patient through a breathing circuit referred to in the industry as a circle system (named because its components are arranged in a circular manner). This system contains a Y type connector with one end connected to the patient's airway (face mask or endotracheal tube) and its other two ends connected to unidirectional inspiratory and expiratory valves. Other circle system components include a canister with carbon dioxide absorbent and a means of inflating and deflating a patient's lungs (i.e. reservoir bag and mechanical ventilator with appropriate pressure alarms and safety valves.)

Concentrations of liquid anesthetic agents such as halothane, isoflurane, sevoflurane, desflurane, and the like, are controlled and administered with temperature-compensated, variable bypass anesthesia vaporizers. Those skilled in the art appreciate that using a variable bypass anesthesia vaporizer allows the anesthesia operator to alter the concentration setting on the vaporizer in order to regulate the amount of gas flowing through the bypass and vaporizing chambers. As gas enters the vaporizer chamber it flows over liquid anesthetic and becomes saturated with vapor. The resulting gaseous mixture passes through the bypass chamber at the vaporizer outlet to produce the desired concentration of anesthetic. These vaporizers are temperature compensated since the saturated vapor pressures are highly dependant on temperature, and evaporation of anesthetic from liquid to gas form would otherwise lead to a cooling of the remaining liquid anesthetic.

Different types of liquid anesthetic agents may require different types of anesthesia vaporizers. For example, desflurane requires a different type of vaporizer than the other liquid anesthetic agents due to its high saturated vapor pressure. The desflurane within the anesthesia vaporizer is heated to about 39° C. and contains a reservoir of desflurane vapor maintained at about 2 lbs/in$^2$ pressure. A vaporizer used with the anesthetic agent halothane may require the volatile anesthetic to be kept at different temperatures and under different pressures.

The administration of inhaled anesthetics must be individualized to each patient's unique requirements. Administration of an inadequate amount of a volatile anesthetic to a patient may produce an inadequate depth of anesthesia and result in anesthetic awareness or recall. Anesthetic awareness or recall ranks among the most common fears a patient experiences prior to undergoing a procedure requiring general anesthesia. Unintended anesthetic recall or awareness occurs under general anesthesia when a patient becomes cognizant of some or all events during surgery or a procedure, and has direct recall of those events. Overall the incidence of awareness during general anesthesia is relatively small, about 1 or 2 per 1000 cases. User error such as machine malfunction, empty vaporizer, syringe swaps, inadequate dosing of drugs, and the like accounts for almost half of these cases.

Recall and awareness under anesthesia still remains a significant problem. At present, medicine lacks an awareness monitor to inform the anesthesia practitioner of the precise moment that a patient will regain consciousness. Since user error such as an empty vaporizer accounts for about half of all anesthetic recall and awareness cases, a vaporizer alarm would provide the anesthesia practitioner with another means of preventing this complication. Embodiments of the present invention provide the anesthesia practitioner with the means to monitor and identify when an anesthesia vaporizer may be empty.

FIG. 1 displays a Ohmeda Fluotec-4 (also referred to as a "Tec-4" vaporizer) anesthesia agent vaporizer 100 currently used in the industry today. The vaporizer 100 is typically installed in an anesthesia machine (not shown for ease of illustration). The anesthesia machine may contain a ventilator to assist the patient's breathing, flow-meters to measure the flow rate of oxygen and nitrous oxide, pulse monitors to monitor the patient's pulse, and the like. Once the vaporizer 100 is installed in the anesthesia machine, the oxygen/nitrous oxide mixture flows into the vaporizer 100 through an intake port. The anesthesia practitioner may adjust the concentration of anesthetic agent by dialing the regulator dial 102 on the top of the vaporizer 100 to the desired percentage concentration. The combined gas and vaporized anesthetic agent exit the vaporizer 100 at an exhaust port.

As mentioned previously, volatile anesthetic agents such as halothane, isoflurane, and sevoflurane may vaporize at room temperature and standard pressure. The vaporizer 100 regulates the amount of vaporization of the volatile anesthetic agents by increasing or decreasing the volume of air flowing through the vaporizer 100. Prior to being vaporized, the volatile anesthetic agent is contained in a reservoir 104 within the vaporizer 100. The vaporizer 100 may be filled by removing the lid 108 and pouring in the liquid anesthetic agent until the desired level is achieved.

On the front of the reservoir 104 is an external indicator 120. The external indicator 120 may consist of a glass tube containing a column of liquid anesthetic agent. The level of the column of liquid anesthetic agent within the external indicator 120 may reflect the level of the liquid anesthetic agent inside the reservoir 104 of the vaporizer 100. The external indicator 120 may be marked with predetermined level indications such as a "full" level indication 122 and an "empty" level indication 124. When the liquid anesthetic agent is added, the anesthesia practitioner uses the full level indication 122 as a guide to keep from overfilling the reservoir 104. Correspondingly, the anesthesia practitioner may use the empty level indication 124 to determine that the vaporizer 100 needs to be refilled.

As the vaporizer 100 is used, the volatile anesthetic agent is slowly vaporized and the level as shown in the external indicator 120 gradually drops from the full level indication 122 towards the empty level indication 124. The anesthesia practitioner typically keeps track of the level of the volatile anesthetic agent in the vaporizer 100 by visually inspecting the external indicator 120. If the level of liquid anesthetic agent within the external indicator 120 drops below the empty level indication 124, the liquid anesthetic agent may be exhausted. If the liquid anesthetic agent is exhausted while the vaporizer 100 is in use, there is a risk that the patient may not get enough anesthetic and may become conscious. Given that the external indicator 120 may be relatively small and difficult to read especially in low level light conditions, the anesthesia practitioner may not notice when the fluid level within the external indicator 120 reaches the empty level indication 124.

Figure 2:
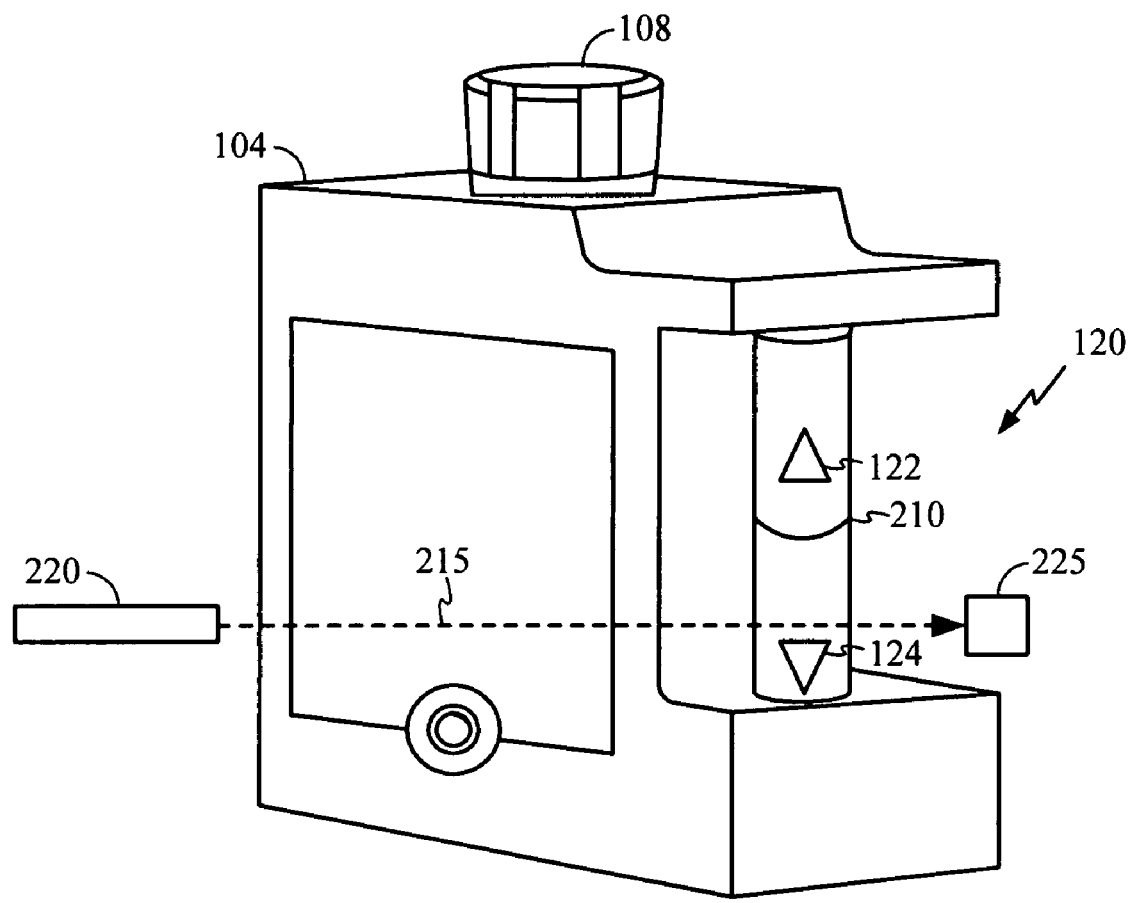
FIG. 2 displays an external indicator of the anesthesia vaporizer of FIG. 1 having an embodiment of the present invention.

FIG. 2 displays a closer view of the external indicator 120 of the vaporizer 100 utilizing one embodiment of the present invention. Within the external indicator 120, the level of fluid may appear parabolic. This is due to a meniscus 210 which forms on the top of the column of fluid. The meniscus 210 is a curve in the surface of the column of liquid anesthetic agent and is produced in response to the surface of the glass tube of the external indicator 120. The meniscus 210 may be either concave or convex, depending on the fluid and the container. As displayed in FIG. 2, the meniscus 210 is a concave meniscus and occurs when the molecules of the liquid anesthetic agent attract those of the glass tube. The meniscus 310 is also displayed in the cross-sectional view of the external indicator 520 of FIGS. 3A-B. Conversely, a convex meniscus occurs when the molecules of the liquid repel the molecules of the container or object. This may be seen between mercury and glass in barometers. The inventive concepts of the present invention may be applied to either a concave or a convex meniscus.

One embodiment of the present invention monitors the level of liquid anesthetic agent within the external indicator 120 of the vaporizer 100 and may trigger an audible and/or a visual alarm when the level of liquid anesthetic agent reaches a predetermined level. By actively monitoring the level of volatile anesthetic agent within the vaporizer 100, the anesthesia practitioner may be made aware of a low level condition and replenish the liquid anesthetic agent prior to running out, thus alleviating the unintended consequence of recall and awareness as previously described.

In an exemplary embodiment, a beam of light 215 may be directed to the external indicator 120 from a light source 220 as is displayed in FIG. 2. The external indicator 120 may be free standing (i.e. isolated from the main body of the vaporizer 100), thus allowing the light source 220 to shine the beam of light 215 into the external indicator 120 at one side of the external indicator 120 and a receptor 225 may be positioned at an opposing end of the external indicator 120 to receive the beam of light 215. The light source 220 and the receptor 225 may be positioned at about 180 degrees from each other. The receptor 225 may in turn be coupled to a detection circuit 330 which may monitor the intensity of the beam of light. In one embodiment, the receptor 225 may be configured to produce an electrical current that is proportional to the amount of light being received. The electrical current may in turn be directed to and monitored by the detection circuit 330. If the intensity of the beam of light 215 received at the receptor 225 diminishes, the electrical current may also diminish. The detection circuit 330 may be configured to trigger an alarm condition if the electrical current dropped below a predetermined electrical current threshold.

Figure 3A:
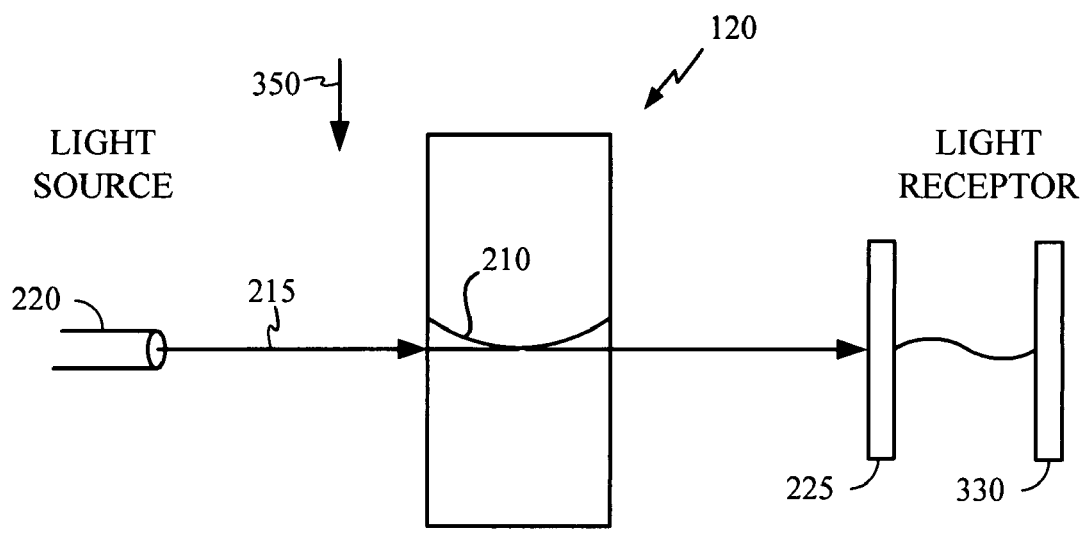
FIG. 3A displays a cross-sectional view of the external indicator of FIG. 2 with the fluid level above the beam of light.
Figure 3B:
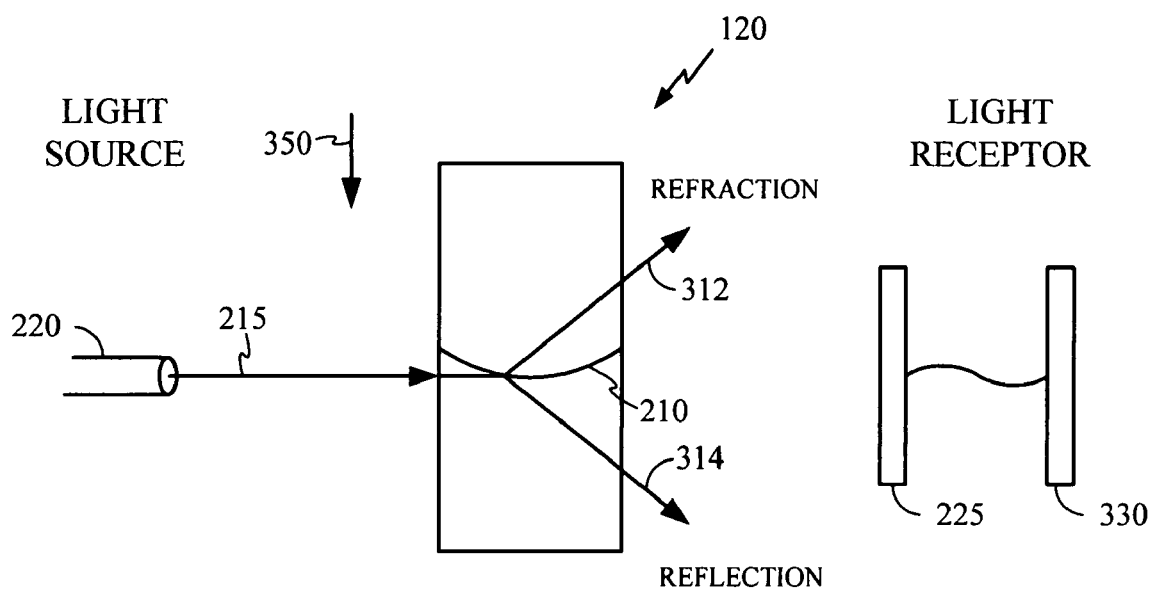
FIG. 3B displays a cross-sectional view of the external indicator of FIG. 2 with the fluid level intercepting the beam of light.

In FIG. 3A, the column of fluid 304 within the external indicator 120 is decreasing in a downward direction 350. As the meniscus 210 crosses the beam of light 215 as shown in FIG. 3B, the beam of light 220 may be split into a refracted component 312 and a reflected component 314, preventing the beam of light 215 from being received at its initial strength at the receptor 225. As mentioned previously, in an exemplary embodiment, an alarm condition may be generated when the receptor 225 detects the change in intensity of the beam of light 215. In one embodiment, the beam of light 215 may be positioned at a predetermined location corresponding to the empty level indication 124. In this embodiment, the alarm condition may continue to exist even after the meniscus 310 falls below the beam of light 215.

As those skilled in the art appreciate, propagation of light waves through different mediums may be understood by referring to Snell's Law (which may also be referred to as Descartes' Law or the law of refraction). Snell's law is a formula used to describe the relationship between the angles of incidence and refraction when referring to light or other waves passing through a boundary between two isotropic media such as glass and air, or in this case air and liquid anesthesia agent. Snell's law states that the ratio of the Sines of the angles of incidence and of refraction is a constant depending on the media. Specifically, the ratio of the sines of the angles of incidence and refraction is equal to the velocities in the two media, or equivalent to the inverse ratio of the indices of refraction. This is shown by the following equation:

$$\frac{\operatorname{Sin}\theta_1}{\operatorname{Sin}\theta_2} = \frac{V_1}{V_2} = \frac{n_1}{n_2}$$

Where $\theta_1$ is the angle from the normal of the incident wave of light and $\theta_2$ is the angle from the normal of the refracted wave of light.

However, when light travels between two mediums, a portion of light may also be reflected away. Predicting the amount of light that is reflected in this instance may be accomplished using Fresnel's equations. Those skilled in the art appreciate that using Fresnel's equation, and knowing what the indicies of refraction for the two media are, one may predict the amount of light that may be both refracted as well as reflected when the light passes between the two media at different angles. As is described in more detail in the discussions of FIGS. 4A-B, embodiments of the present invention detect when the amount of light received at the receptor changes due to the light refracting and reflecting off the meniscus.

Figure 4A:
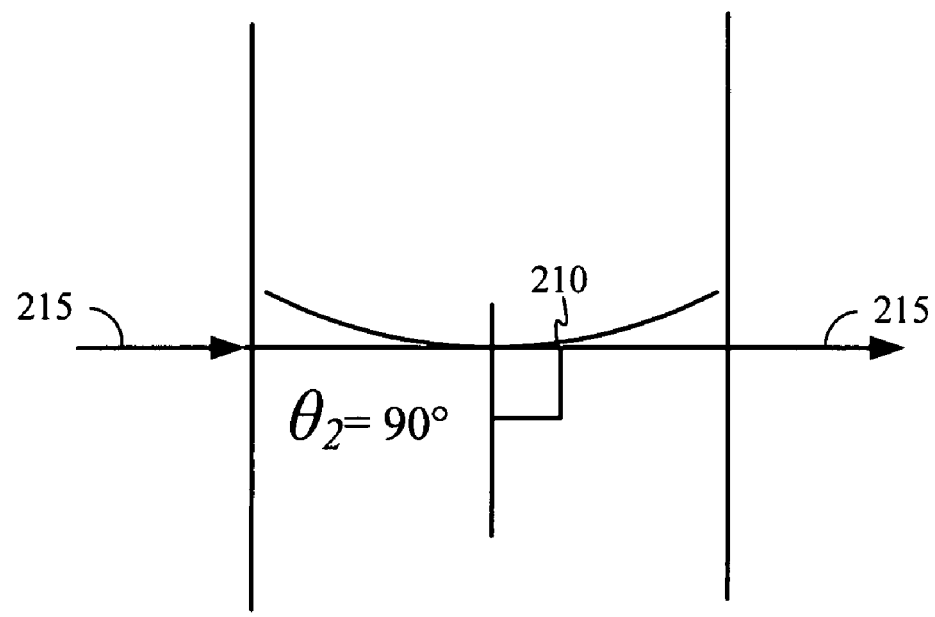
FIG. 4A displays an illustration of the meniscus above the beam of light in the external indicator of FIG. 2.
Figure 4B:
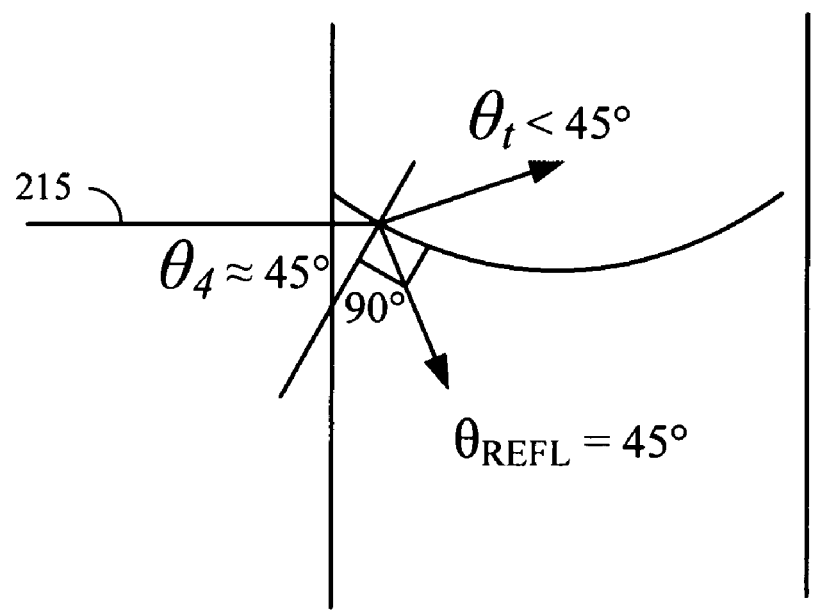
FIG. 4B displays an illustration of the meniscus interacting with the beam of light of the external indicator of FIG. 2.

FIGS. 4A and 4B display a more detailed view of the column of fluid within the external indicator 120 and relate to FIGS. 3A and 3B respectively. In FIG. 4A, the beam of light 215A has not yet reached the meniscus. As a result, the angle of incidence ($\theta_2$) is 90 degrees and relatively little light from the beam of light 215 is reflected or refracted away from the receptor. When the meniscus 210 is above the beam of light 215 (as displayed in FIG. 4A), the beam of light 215 is received at a calibrated strength.

As displayed in FIG. 4B, once the meniscus 210 begins to intersect the beam of light 215, a certain amount of light energy will be reflected as well as refracted away. Specifically, when the angle of incidence ($\theta_4$) between the beam of light 215 and the meniscus 210 is about 45 degrees, a portion of the beam of light 215 is reflected at an angle ($\theta_{REFL}$) of about 45 degrees and another portion of the beam of light 215 is refracted at an angle ($\theta_r$) which may be less than 45 degrees. As a result of the reflection and refraction, very little light may be received at the receptor 225. When this condition occurs, the detection circuit 330 detects the loss of intensity of the beam of light 215 and may activate an alarm condition.

When the detection circuit 330 has determined that an alarm condition exists, the detection circuit 330 may be configured to activate a visual alarm. For example, the detection circuit 330 may activate a flashing light on the anesthesia vaporizer 100. Alternatively, the detection circuit 330 may be coupled with the anesthesia machine and be configured to activate a visual alarm on the anesthesia machine display. In yet another alternative embodiment, the detection circuit 330 may be configured to activate an audible alarm. The audible alarm may be as simple as a periodic beep or it may be a louder constant audible alarm. In another alternative embodiment, the detection circuit may be configured to activate both an audible and a visual alarm.

After the alarm condition is activated, the detection circuit 330 may be configured to reset after manual intervention has occurred. For example, the detection circuit 330 may reset the alarm condition after the anesthesia practitioner has refilled the anesthesia vaporizer 100 with enough anesthetic agent to bring the fluid level in the external indicator above the empty designation 124. In an alternative embodiment, another light source, receptor and detection circuit may be added to the external indicator 120 to detect when the fluid level in the external indicator 120 is at the full designation 122. In this configuration, the detection circuit 330 may reset the alarm condition once it has detected that the meniscus 210 has reached the full designation 122. Lastly, the detection circuit 330 may be manually reset by the anesthesia practitioner, denoting recognition of the alarm condition.

Figure 5:
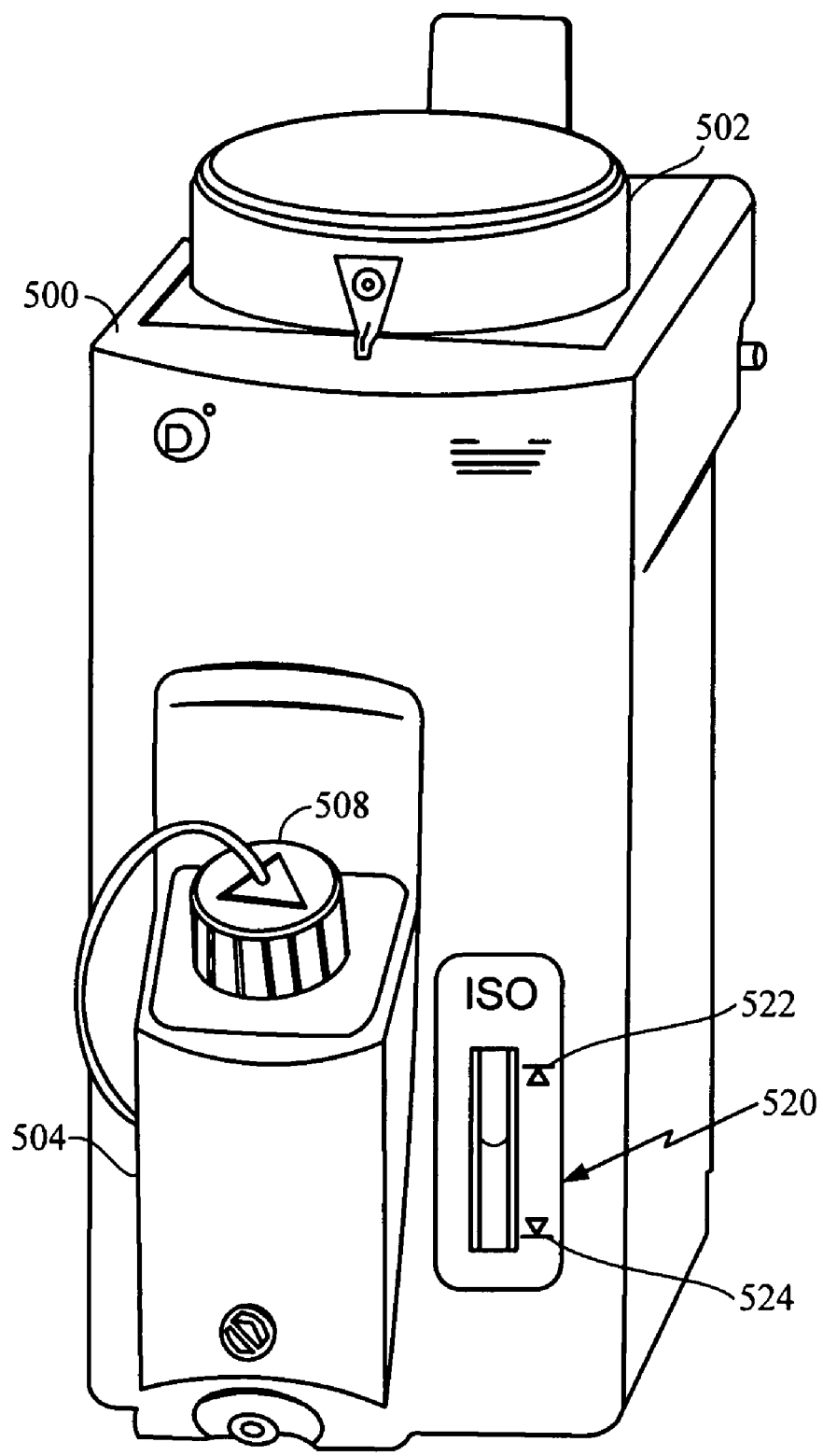
FIG. 5 displays a Tec-7 anesthesia vaporizer.

The same principles as mentioned previously may be applied to other types of anesthesia vaporizers. One such vaporizer 500 as displayed in FIG. 5 is an Ohmeda Fluotec-7 (commonly referred to in the industry as a "Tec-7") anesthesia vaporizer. The vaporizer 500 may be similar to the vaporizer 100 of FIG. 1 and has a regulator dial 502 on the top of the vaporizer 500 which may be adjusted by the anesthesia practitioner to the desired percentage concentration. On the front of the vaporizer 500 is an external indicator 520 which may reflect the amount of anesthetic agent within a reservoir 504. Similar to the external indicator 120, the external indicator 520 may be a glass tube which contains a portion of the volatile anesthetic agent. The external indicator 520 may be marked with predetermined level indications such as a "full" level indication 522 and an "empty" level indication 524. When the liquid anesthetic agent is added, the anesthesia practitioner removes the lid 508 and adds the anesthetic agent directly into the reservoir 504. Typically the anesthesia practitioner uses the full level indication 522 as a guide to keep from overfilling the reservoir 504. Correspondingly, the anesthesia practitioner uses the empty level indication 524 to determine that the vaporizer 500 needs to be refilled.

Figure 6:
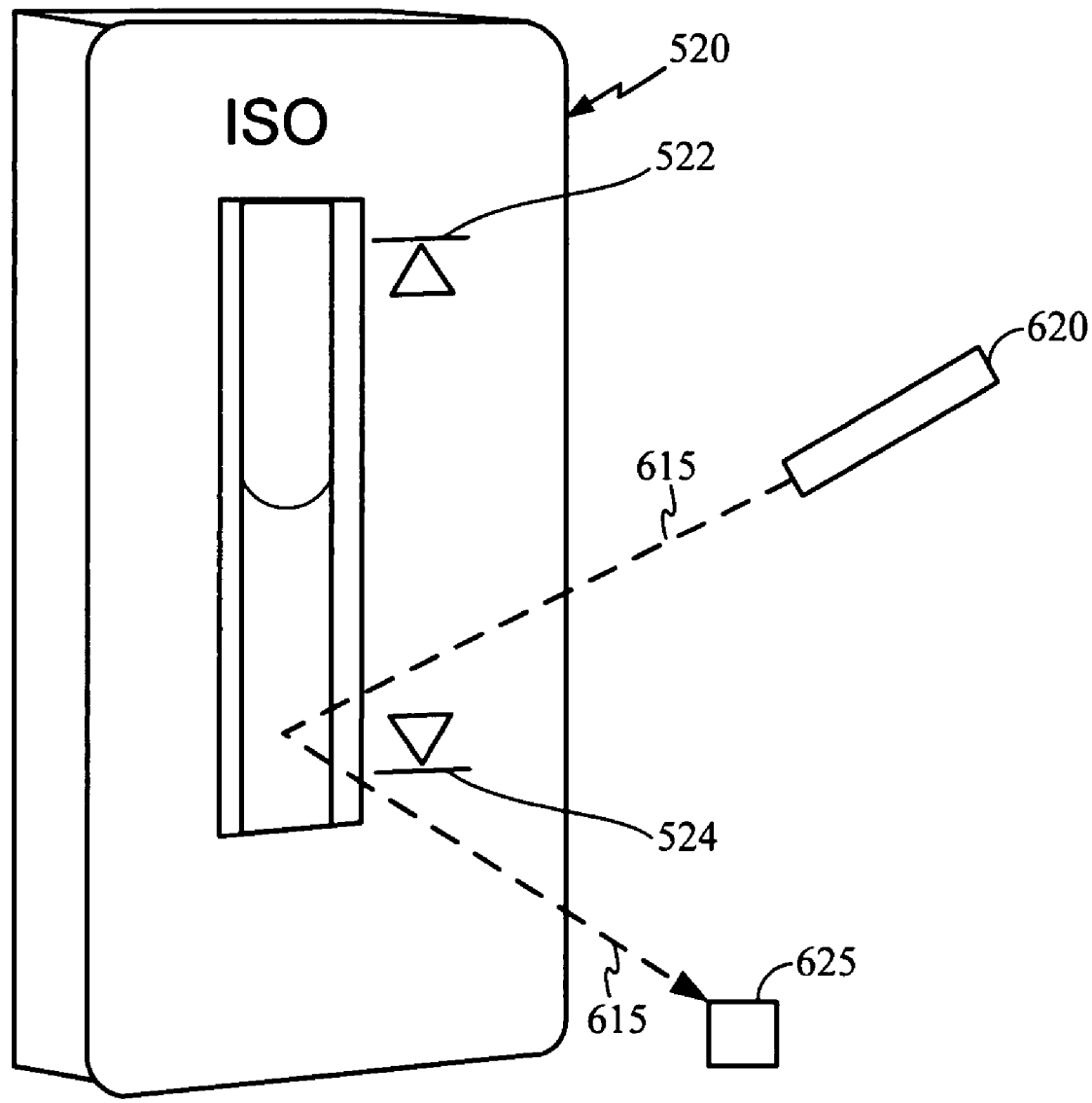
FIG. 6 displays an external indicator of the anesthesia vaporizer of FIG. 5 having another embodiment of the present invention.

FIG. 6 displays a close up view of the external indicator 520 of the vaporizer 500. As can be seen in FIGS. 5-6, the vaporizer 500 has an external indicator 520 that is not isolated from the body of the vaporizer 500, in contrast to the vaporizer 100 of FIG. 1. The external indicator 520 of the vaporizer 500 is integrated into the body of the vaporizer 500 and has a glass tube positioned behind a transparent plastic screen. The transparent plastic screen provides a protected environment for the external indicator 520. Because the external indicator 520 is not isolated from the vaporizer 500, a light source 620 and a light receptor 625 may not be positioned at opposing ends (at about 180 degrees from each other) as is shown in FIGS. 2-4. For the vaporizer 500, other embodiments of the present invention may be adapted to be used with a non isolated external indicator 520. One embodiment of the present invention may utilize a reflectance method to determine the level of liquid anesthetic agent contained within the external indicator 520 of the vaporizer 500.

Similar to the external indicator 120, the external indicator 520, may contain a column of liquid anesthetic. The column of liquid anesthetic agent may correspond to the level of liquid anesthetic agent contained within the reservoir 504. As the vaporizer 500 is used, the liquid anesthetic agent is slowly vaporized and the level as shown in the external indicator 520 gradually drops from the full level indication 522 towards the empty level indication 524. As mentioned previously, the anesthesia practitioner keeps track of the level of the liquid anesthetic agent in the vaporizer 500 by visually inspecting the external indicator 520. If the level of liquid anesthetic agent within the external indicator 520 drops below the empty level indication 524, the liquid anesthetic agent may be exhausted. If the liquid anesthetic agent is exhausted while the vaporizer 500 is in use, there is a risk that the patient may not get enough anesthetic and may become conscious. Given that the external indicator 520 may be relatively small and difficult to read especially in low level light conditions, the anesthesia practitioner may not notice when the fluid level within the external indicator 520 reaches the empty level indication 524.

Figure 7A:
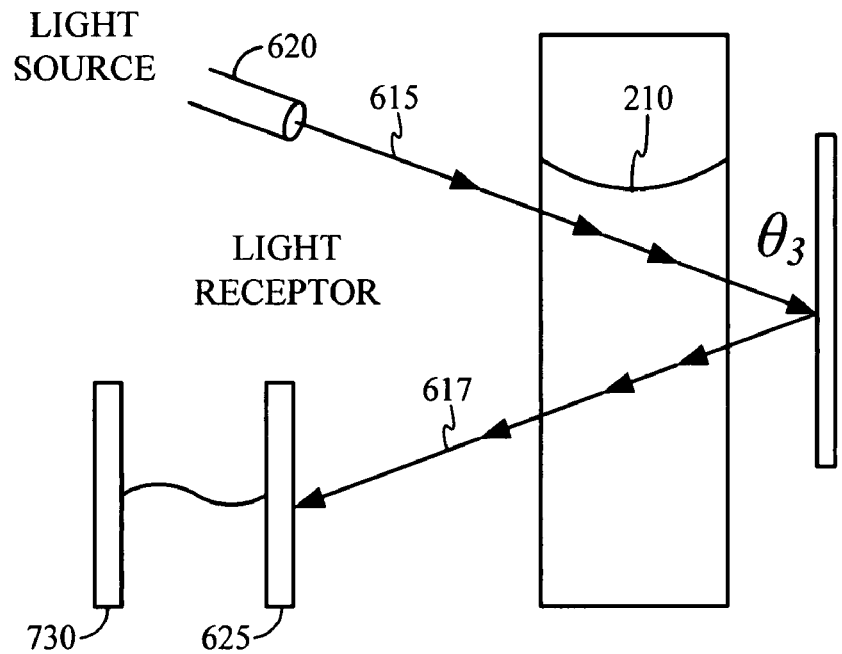
FIG. 7A displays a cross-sectional view of the external indicator of FIG. 6 utilizing an embodiment of the present invention with the fluid level above the beam of light.
Figure 7B:
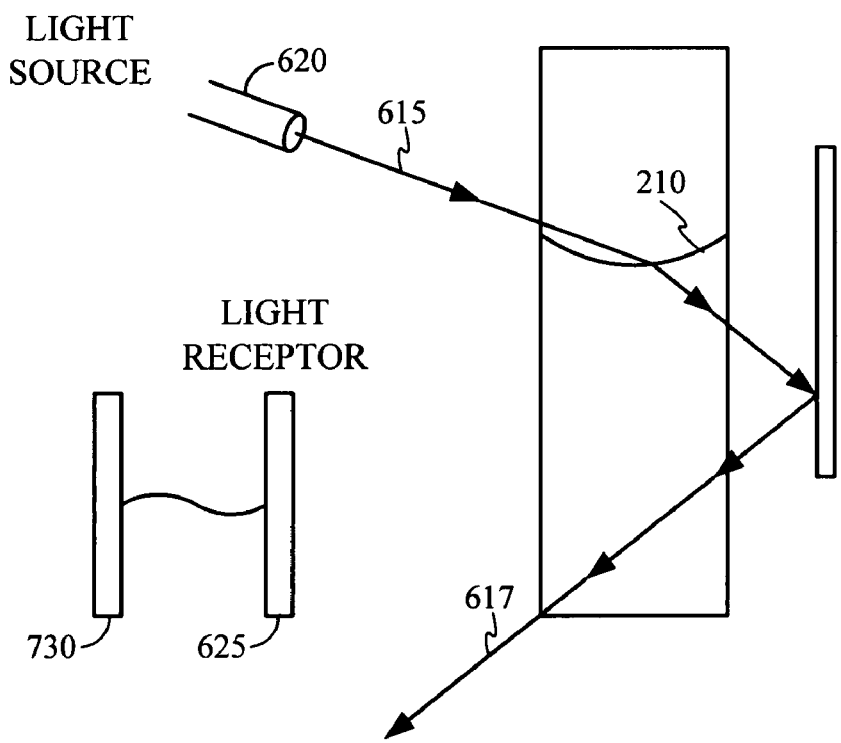
FIG. 7B displays a cross-sectional view of the external indicator of FIG. 6 utilizing an embodiment of the present invention with the fluid level intersecting the beam of light.

FIGS. 7A-B display a cross-sectional view of the external indicator 520 utilizing another embodiment of the present invention. As shown in FIG. 7A, a light source 620 directs a beam of light 615 into the external indicator 520. In one exemplary embodiment, the beam of light 615 is directed at about a 45 degree angle ($\theta_3$). Transmitted from the back of the external indicator 520, a beam of reflected light 617 continues through the liquid anesthetic agent and is received at the light receptor 625. The light receptor 625 in turn is coupled to a detection circuit 730. In the embodiment of FIG. 7, the light receptor 625 is positioned to receive the reflected beam of light 617. Similar to the light receptor 325 of FIG. 3, the light receptor 625 may produce an electrical current that is proportional to the intensity of the light received. The detection circuit 730 receives and monitors the electrical current produced by the receptor 625. If the amount of light received at the receptor 625 diminishes, the electrical current produced and sent to the detection circuit 730 may also diminish. As a result, the detection circuit 730 may be configured to trigger an alarm condition when the intensity of the reflected beam of light 617 diminishes.

FIG. 7B shows the meniscus 210 within the external indicator 520 coming into contact with the beam of light 615. In this instance, the beam of light 615 may be refracted and or reflected away from the receptor 625. One embodiment of the present invention detects when the meniscus 210 of the liquid anesthesia agent drops below a predetermined level. When the meniscus 210 is detected, the intensity of the reflected beam of light 617 diminishes and the detection circuit 730 triggers an alarm condition. As mentioned previously, when the detection circuit 730 has determined that an alarm condition exists, the detection circuit 730 may be configured to activate a visual alarm. For example, the detection circuit 730 may activate a flashing light on the anesthesia vaporizer 500. Alternatively, the detection circuit 730 may be coupled with the anesthesia machine and be configured to activate a visual alarm on the anesthesia machine display. In yet another alternative embodiment, the detection circuit 730 may be configured to activate an audible alarm. The audible alarm may be as simple as a periodic beep or it may be a louder constant audible alarm. In another alternative embodiment, the detection circuit may be configured to activate both an audible and a visual alarm.

After the alarm condition is activated, the detection circuit 730 may be configured to reset after manual intervention has occurred. For example, the detection circuit 730 may reset the alarm condition after the anesthesia practitioner has refilled the anesthesia vaporizer 500 with enough liquid anesthetic to bring the fluid level in the external indicator 520 above the empty designation 524. In an alternative embodiment, another light source, receptor and detection circuit may be added to the external indicator 520 to detect when the fluid level in the external indicator 520 is at the full designation 522. In this configuration, the detection circuit 730 may reset the alarm condition once it has detected that the meniscus 210 has reached the full designation 522.

Embodiments of the present invention may be utilized as an aftermarket addition to existing anesthetic agent vaporizers. Several designs of vaporizers are currently being used in practice both in the U.S., and abroad. Older anesthesia vaporizers are similar to the anesthesia vaporizer 100 as displayed in FIGS. 1-2. Newer anesthesia vaporizers are similar to the vaporizer 500 of FIGS. 5-6. Alternatively, embodiments of the present invention may be applied to brand new anesthesia vaporizers. In addition, the inventive concepts as presented herein may also be applied to all transmitted wavelengths of light, all transverse waves in general, and also to longitudinal waves (i.e., sound and ultrasonic waves).

Although specific embodiments have been illustrated and described herein, those of ordinary skill in the art appreciate that any arrangement, which is calculated to achieve the same purpose, may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A method of detecting a level of anesthetic agent in an anesthesia vaporizer, the anesthetic agent forming a column of liquid anesthetic agent within an external indicator, the external indicator positioned adjacent to the anesthesia vaporizer, the external indicator coupled to the anesthesia vaporizer, the external indicator composed of material allowing the column of liquid to be detectable, the column of liquid being indicative of an amount of anesthetic agent contained within the anesthesia vaporizer, the method comprising:
   projecting a beam of light into the external indicator,
   receiving the beam of light after the beam of light has traveled through the external indicator,
   detecting when the column of liquid reaches a predetermined level.

2. The method of claim 1 wherein the column of liquid has a meniscus and the step of detecting the level of anesthetic agent further comprises detecting when the meniscus passes below the predetermined level.

3. The method of claim 2 wherein the meniscus causes the beam of light to alter its path through the external indicator.

4. The method of claim 1 wherein the beam of light is received at an opposing side of the external indicator.

5. The method of claim 1 wherein the beam of light is projected and received at a projection side of the external indicator.

6. The method of claim 5 wherein the beam of light is reflected off an opposite side of the external indicator.

7. The method of claim 1 wherein the beam of light is a laser beam.

8. An apparatus for detecting a level of an anesthetic agent in an anesthesia vaporizer when the apparatus is coupled to an external indicator of the anesthesia vaporizer, the external indicator positioned adjacent to the anesthesia vaporizer, the external indicator coupled to the anesthesia vaporizer, the external indicator composed of material allowing a column of liquid anesthetic agent contained therein to be detectable, the column of liquid being indicative of a level of the anesthetic agent contained within the anesthesia vaporizer, the apparatus comprising:

a light source for emitting a beam of light into the external indicator;

a light receptor for receiving the beam of light after the beam of light has traveled through the external indicator; and a detection logic circuit for detecting when the beam of light is altered when the column of liquid reaches a predetermined level.

9. The apparatus of claim 8 wherein the light source and the light receptor are at opposing sides of the external indicator.

10. The apparatus of claim 8 wherein the light source and the light receptor are at the same sides of the external indicator.

11. The apparatus of claim 10 wherein the beam of light is reflected off an opposite side of the external indicator.

12. The apparatus of claim 8 wherein the detection logic circuit detects when a meniscus formed within the external indicator reaches the predetermined level.

13. The apparatus of claim 12 wherein the meniscus causes the beam of light to be altered.

14. The apparatus of claim 8 wherein the beam of light is a laser beam.

15. An anesthesia vaporizer comprising:

an external indicator positioned adjacent to the anesthesia vaporizer, the external indicator coupled to the anesthesia vaporizer, the external indicator comprising a column of liquid anesthetic agent, the column of liquid being proportional to an amount of anesthetic agent contained within the anesthesia vaporizer, the external indicator composed of material allowing the column of liquid to be detectable;

a light source emitting a beam of light, the light source coupled to the external indicator;

a light receptor, the light receptor configured to receive the beam of light after the beam of light travels through the external indicator;

a detection logic circuit, the detection logic circuit detecting when the column of liquid anesthetic agent reaches a predetermined level.

16. The anesthesia vaporizer of claim 15 wherein the light source and the light receptor are at opposing sides of the external indicator.

17. The anesthesia vaporizer of claim 15 wherein the light source and the light receptor are at the same side of the external indicator.

18. The anesthesia vaporizer of claim 17 wherein the beam of light is reflected off an opposing side of the external indicator.

19. The anesthesia vaporizer of claim 15 wherein the detection logic circuit detects when a meniscus formed within the external indicator reaches the predetermined level.

20. The anesthesia vaporizer of claim 15 wherein the material is glass.

21. The anesthesia vaporizer of claim 15 wherein the light source emits a laser beam.

* * * * *